US010206609B2

(12) United States Patent
Alberts et al.

(10) Patent No.: US 10,206,609 B2
(45) Date of Patent: *Feb. 19, 2019

(54) OBJECT RECOGNITION BY TOUCH SCREEN

(71) Applicant: THE CLEVELAND CLINIC FOUNDATION, Cleveland, OH (US)

(72) Inventors: Jay L. Alberts, Chagrin Falls, OH (US); David D. Schindler, Russell, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,320

(22) Filed: Aug. 8, 2017

(65) Prior Publication Data
US 2017/0332949 A1 Nov. 23, 2017

Related U.S. Application Data

(63) Continuation of application No. 14/503,928, filed on Oct. 1, 2014, now Pat. No. 9,737,242.
(Continued)

(51) Int. Cl.
*G06F 3/041* (2006.01)
*G06F 3/0354* (2013.01)
(Continued)

(52) U.S. Cl.
CPC ........ *A61B 5/1124* (2013.01); *A61B 5/04001* (2013.01); *A61B 5/4082* (2013.01); *A61B 5/4088* (2013.01); *G06F 3/03545* (2013.01); *G06F 3/044* (2013.01); *G06F 3/0416* (2013.01); *A61B 5/1101* (2013.01); *A61B 5/162* (2013.01)

(58) Field of Classification Search
None
See application file for complete search history.

(56) References Cited

U.S. PATENT DOCUMENTS 5,283,558 A * 2/1994 Chan .................. G06F 3/045
178/18.05
5,572,573 A * 11/1996 Sylvan ............... H04M 1/0266
341/23

(Continued)

OTHER PUBLICATIONS

Anonymous: "Operation Ilmagel BoardGameGeek", Jan. 1, 1965, http://boardgamegeek.com/image/190365/operation, Figure.
(Continued)

*Primary Examiner* — Kent W Chang
*Assistant Examiner* — Nathaniel P Brittingham
(74) *Attorney, Agent, or Firm* — Tarolli, Sundheim, Covell & Tummino LLP

(57) ABSTRACT

Devices, systems and methods are described that can facilitate recognition of an engagement between an object and a touch screen in the absence of human contact. Upon the engagement, an electrically conductive path can be established that extends from a surface of the touch screen such that sufficient electrons flow from the touch screen through the electrically conductive path to enable the recognition of the object on the touch screen in the absence of human contact with the object during continued presence of the object on the touch screen.

20 Claims, 8 Drawing Sheets

Related U.S. Application Data

(60) Provisional application No. 61/885,193, filed on Oct. 1, 2013.

(51) Int. Cl.
*A61B 5/11* (2006.01)
*G06F 3/044* (2006.01)
*A61B 5/00* (2006.01)
*A61B 5/04* (2006.01)
*A61B 5/16* (2006.01)

(56) References Cited

U.S. PATENT DOCUMENTS

| | | | | |
|---|---|---|---|---|
| 7,173,439 | B1* | 2/2007 | Campbell | G01R 1/06705 |
| | | | | 324/750.25 |
| 7,993,201 | B2* | 8/2011 | Matsumoto | A63F 13/42 |
| | | | | 345/173 |
| 2005/0194984 | A1* | 9/2005 | Chiang | G01R 31/046 |
| | | | | 324/756.02 |
| 2006/0072298 | A1* | 4/2006 | Ng | H05K 1/0224 |
| | | | | 361/818 |
| 2006/0172266 | A1* | 8/2006 | Rogers | G09B 21/00 |
| | | | | 434/112 |
| 2007/0025877 | A1* | 2/2007 | Hansen | A61B 5/7475 |
| | | | | 422/68.1 |
| 2008/0238879 | A1* | 10/2008 | Jaeger | G06F 3/03545 |
| | | | | 345/173 |
| 2009/0241701 | A1* | 10/2009 | Pan | G06F 3/041 |
| | | | | 73/865.9 |
| 2010/0019918 | A1* | 1/2010 | Avital | A61B 18/02 |
| | | | | 340/686.4 |
| 2010/0191236 | A1* | 7/2010 | Johnson | A61N 1/3718 |
| | | | | 606/41 |
| 2012/0092812 | A1* | 4/2012 | Lewis | A61B 5/14532 |
| | | | | 361/679.01 |
| 2012/0327013 | A1 | 12/2012 | Lee et al. | |
| 2012/0327041 | A1* | 12/2012 | Harley | G06F 3/03545 |
| | | | | 345/179 |
| 2014/0092055 | A1* | 4/2014 | Radivojevic | G06F 3/016 |
| | | | | 345/174 |
| 2014/0145967 | A1* | 5/2014 | Edwards | G06F 1/1628 |
| | | | | 345/173 |
| 2014/0278187 | A1* | 9/2014 | Rovito | G06F 3/0418 |
| | | | | 702/104 |
| 2014/0306929 | A1* | 10/2014 | Huang | G06F 3/03545 |
| | | | | 345/174 |
| 2015/0094621 | A1* | 4/2015 | Alberts | A61B 5/1124 |
| | | | | 600/595 |
| 2016/0302710 | A1* | 10/2016 | Alberts | A61B 5/112 |

OTHER PUBLICATIONS

Rudick et al. The Multiple Sclerosis Performance Test (MSPT): An iPad-Based Disability Assessment Tool. J. Vis. Exp. (88), e51318, doi:10.3791/51318 (2014). Video.

International Search Report and Written Opinion for PCT/US2014/058608, dated Dec. 19, 2014, pp. 1-13.

* cited by examiner

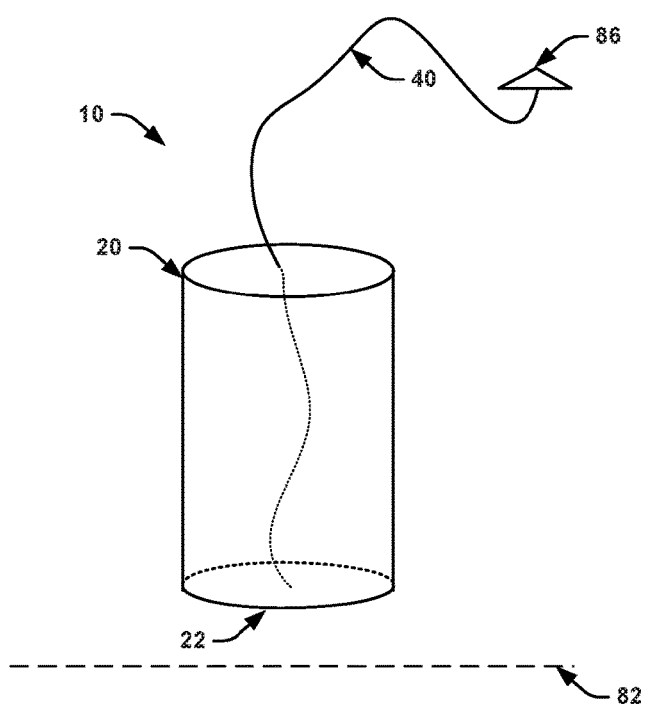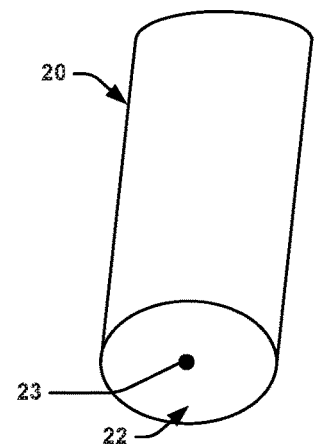
FIG. 1  FIG. 2

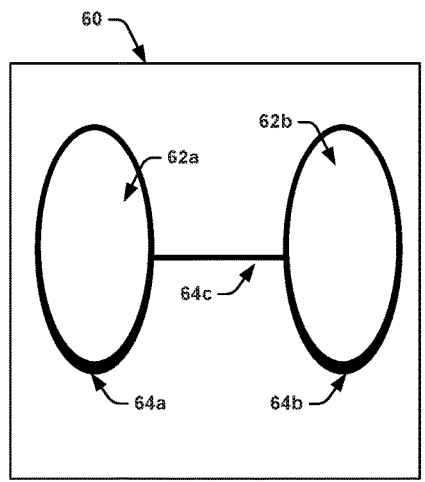 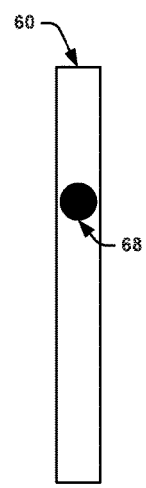 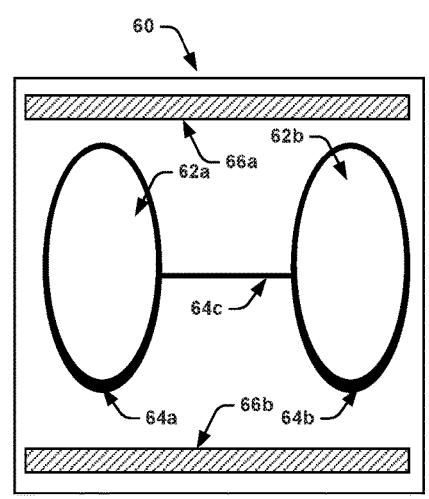
FIG. 11   FIG. 12   FIG. 13

OBJECT RECOGNITION BY TOUCH SCREEN

CROSS-REFERENCE TO RELATED APPLICATION

This application is a continuation of U.S. patent application Ser. No. 14/503,928, filed Oct. 1, 2014, which claims the benefit of U.S. Provisional Patent Application No. 61/885,193, filed Oct. 1, 2013 and entitled OBJECT RECOGNITION BY TOUCH SCREEN. The subject matter of these applications is incorporated herein in its entirety.

TECHNICAL FIELD

This disclosure relates generally to devices, systems and methods to enable an object to be detected by a touch screen in the absence of human contact.

BACKGROUND

Various user input devices can provide an interactive surface configured to receive user inputs. For example, a touch screen or touch-sensitive pad can be used as input devices to different computing devices, including tablet computing devices, mobile phones, and laptop computing devices. As a further example, capacitive touch screens can detect an input when a human body (or a conductive object contacting the human body) touches the screen, but not when a non-conductive object touches the screen. This distinction is generally due to the electrical characteristics of the human body that can change the capacitance of the screen.

BRIEF DESCRIPTION OF THE DRAWINGS

FIGS. 1 and 2 depict an example configuration of an object that can be detected by a touch screen in the absence of human contact.

FIGS. 11-13 depict an example configuration of the housing with two apertures.

DETAILED DESCRIPTION

Figure 3:
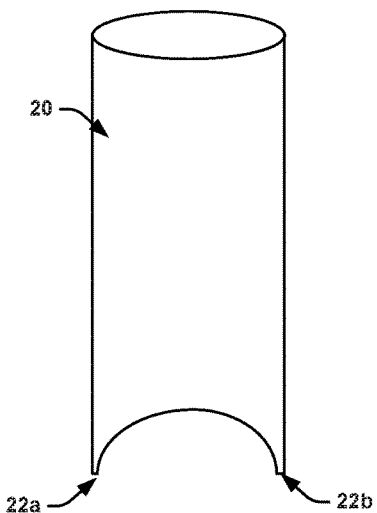
FIGS. 3-5 depict example configurations of the contact surface of the object that can engage with a corresponding surface of the touch screen.

This disclosure relates to devices, systems and methods to enable a touch-sensitive surface (e.g., a touch screen, a touch pad or the like) to detect an object in the absence of direct human contact. When the object engages with the touch-sensitive surface with or without human contact, an electrically conductive path can be established extending from the touch-sensitive surface. The path can establish a sufficient flow of electrons to enable the electrical characteristics (e.g., capacitance) of the touch-sensitive surface to change so that the engagement can be detected even in the absence of human contact.

The devices systems and methods are particularly suitable for implementing a quantitative test for assessing and/or diagnosing neurological and/or neurocognitive disorders. As an example, a nine-hole peg or similar test device can include a housing that is placed on to a touch-sensitive surface and include a plurality of holes into which pegs or other objects can be inserted by a user. Since the object can be detected by the touch-sensitive surface in the absence of contact by the subject, based on an electrically conductive path that is established when a given peg is inserted into a hole to contact the touch-sensitive surface, each peg can be detected during the test even after it is released by the user. As a result, the touch screen interface and associated processor can be programmed to quantify the results of the test to help diagnose and assess a patient's condition.

The device, system and methods disclosed herein used in conjunction with a computing device enable both assessment of quantity of movement as well as quality of movements. Moreover, each task performed can be evaluated individually and can be combined as a series for aggregate evaluation. This further make possible at-home or off-site testing for tests that typically need to be administered by trained technicians. For sake of consistency, in the following examples, the touch-sensitive surface is described as surface of touch screen.

FIG. 1 depicts an example device 10 that includes an object 20 that includes a contact surface 22 that is configured to engage a surface of touch screen. For example the contact surface can be one or more ends or other surface portion thereof. The object 20 is further configured to establish an electrically conductive path 40 that extends from the contact surface 22, along or though the object to a termination end of the path. Thus, when a contact surface 22 of the object 20 engages a corresponding surface 82 of a touch screen, the touch screen (or device associated with the touch screen) can detect the engagement, even in the absence of human contact.

As shown in examples of FIGS. 1 and 2, the object 20 can include a body portion having a cylindrical shaped sidewall extending between opposing ends of the body. At least a portion of one of the ends of the body of the object 20 defines the contact surface 22 that is configured to engage a corresponding surface 82 of the touch screen. In the example of FIG. 2 the contact surface 22 of the object includes a protrusion (e.g., a nipple) 23 that extends axially outwardly from the end surface, such as from a generally central portion of the surface for engaging a touch screen. Additionally, the body of object 20 can be solid, hollow or any combination of solid and hollow.

Although the object 20 is illustrated as a right circular cylinder herein, it will be understood that such shape is shown only as an example of a possible shape for the object 20. The object 20 can have other cylindrical shapes as well as be a disk shape, for example, with a minimal intermediate sidewall portion (e.g., a short sidewall that is less than the diameter). In other examples, the object 20 can be a pyramidal shape, a spherical shape, an irregular three dimensional shape (e.g., a chess piece), an irregular two dimensional shape or another shape (e.g., a flat object such as a sticker or a disc) that can include the contact surface 22 that can engage with the corresponding screen surface 82.

Figure 4:
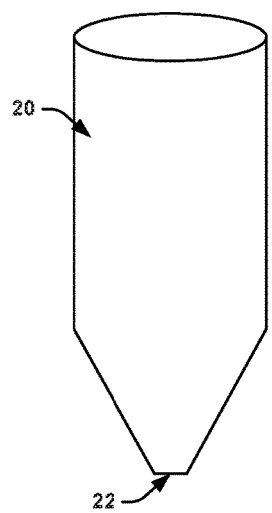
Figure 5:
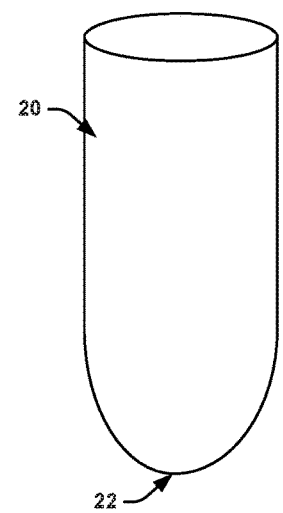

As shown in FIGS. 1 and 2, the contact surface 22 can be a generally planar surface that provides for flat mating engagement with the touch screen surface as to hold the object in an upright position relative to the touch screen. In other examples, the contact surface need not be flat, such as shown in FIGS. 3-5, which depict examples of contoured configurations of the contact surface 22, which might provide imbalance and urge the object to fall over when placed on a flat surface. In the example of FIG. 3, the contact surface 22a and/or 22b can be a convex end portion extending axially from an end of the object 20. As depicted in the example of FIG. 4, the contact surface 22 of object 20 can include a nipple shape (with a flat surface, as shown, or with, a non-flat surface such as pointed surface, a convex surface or concave surface. As depicted in the example of FIG. 5, the contact surface 22 of object 20 can be a convex shape. The examples shown in FIGS. 1-5 are not meant to be limiting; the contact surface 22 can be of a different shape than the shapes illustrated as long as the engagement with the corresponding surface 82 of the touch screen can be maintained (including maintaining the engagement with the support of a housing device) for at least a time period sufficient for detection. As disclosed herein, regardless of the configuration, the contact surface includes an electrically conductive portion configured to engage the touch screen, which electrically conductive portion is coupled to the termination end 86 via the electrically conductive path. Different lengths and configurations can be used for the path, as disclosed herein. Different types of termination ends can also be utilized, such as depending on if the end 86 is to remain in free space or couple with a surface or plug into a connector port.

By way of example, referring back to FIGS. 1 and 2, the contact surface 22 includes an electrically conductive portion of that establishes the electrically conductive path 40 upon the engagement of the contact surface 22 with the corresponding surface 82 of the touch screen. The electrically conductive portion together with the path are sufficient to alter capacitance such that the touch screen can detect the object 20 engagement. As one example, the electrically conductive portion can be a size of a wire. As another example, the electrically conductive portion can be the entire contact surface 22. The electrically conductive portion can include a conductive material, such as a metal (e.g., aluminum, stainless steel, gold, platinum, etc.), an electrically conductive foam, an electrically conductive rubber, or other electrically conductive materials.

When the contact surface 22 engages with the corresponding surface 82 of the touch screen, an electron flow (e.g., low level current) can be established through the electrically conductive path 40 extending from the electrically conductive portion at the contact surface of the object 20. For the example of a capacitive touch screen, the electron flow is established through the electrically conductive path 40 in an amount sufficient to evoke a change in electrical properties of the touch screen for the engagement to be detected by the touch screen. For instance, the electrically conductive path 40 extending from the point of contact with the touch screen surface can be configured to cause a change in capacitance at the touch screen in response to contact by the object.

As an example, the electrically conductive path can correspond to a length (e.g., about 5 inches or more) and terminate in a free end 86 that provides a path for flow of electrons from the contact surface 22 of the object. In such example, the path can terminate in air but be of sufficient length to establish a change in capacitance with respect to the touch screen when the object engages the touch. As another example, the electrically conductive path 40 can extend from the contact surface 22 to a physical electrical ground 86, such as a port of the touch screen device, an earth ground source, the human user or a case of the touch screen device.

As yet another example, the contact surface 22 can be electrically connected with a contact 24 of the object 20. The contact 24 can be configured to physical interface with a corresponding contact of another device (see, e.g., housing 60 of FIG. 10) to create a portion of the electrically conductive path 40 from the touch screen and through the object 20. Examples of contact 24 are illustrated in FIGS. 6-9.

Figure 6:
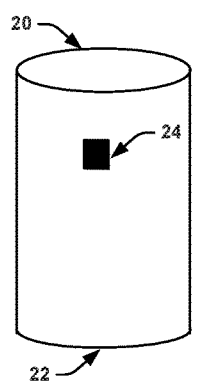
FIGS. 6-9 depict example configurations of a contact on an external surface of the object that can interface with a contact on a surface of an aperture of a housing.
Figure 7:
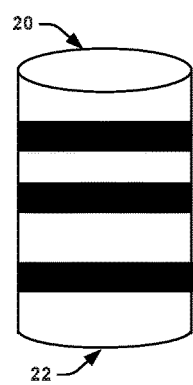
Figure 8:
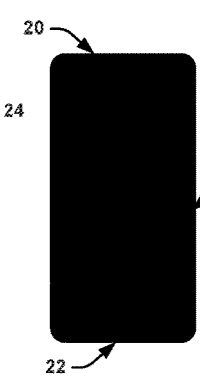

As shown in FIG. 6, the contact 24 can be included on a portion of an outer surface of the body of the object 20. It will be understood that the contact 24 can also include a plurality of discrete contacts distributed axially along the exterior surface of the body of the object of the type as depicted in FIG. 6. As shown in FIG. 7, the contact 24 can be a conductive material wrapped or coiled around the sidewall of the object 20. For example, the contact 24 can be a conductive bushing that is electrically connected with the contact surface. In some instances, the object 20 need not touch (e.g., make physical contact with) the contact 24. For example, a small air gap or a piece of dielectric material can separate the object 20 from the contact 24 turning the object from a conductor physically connected to the contact 24 to a capacitor that does not touch the contact, but instead is separated from the contact by a dielectric. In this example embodiment, one side of the capacitor (the object 20) can be conductively linked to the touch screen and the other side of the capacitor (the contact 24) can be electrically grounded with respect to the touch screen.

As used herein, it is understood that the surface of the touch screen can refer to the actual physical surface of the touch screen or it can refer to one or more layers of a coating or film that may be provided onto or supported over the screen (e.g., supported by the housing or other frame that is placed onto the touch screen surface) or otherwise secured to the touch screen. For example, the one or more layers of coating or film can be formed of an electrically conductive material. The layer of electrically conductive material can be mechanically suspended above the screen in its normal state so as not to contact the screen. The layer of electrically conductive material can be sufficiently pliant to be biased into engagement with the screen surface when an object (e.g., the object 20, such as a peg) is placed on the layer of electrically conductive material. As an example, the layer could be implemented as a stretchable sheet of a material, such as a woven or non-woven fabric material that exhibits high elasticity, such as spandex or elastane, although other elastic panels of conformable material can be utilized (e.g., similar to that used in some athletic clothing or pantyhose). The stretchable fabric layer can be formed of a synthetic, natural or combination of synthetic and natural materials, which itself can be electrically conductive or which can be coated with an electrically conductive material. The layer of material is sufficiently pliant that the mass/weight of the object can itself urge the layer of electrically conductive material into engagement with the touch screen. The layer of electrically conductive material can be connected to an electrical ground as disclosed herein, to provide an electrically conductive path extending from the corresponding surface of the touch screen for flow of electrons sufficient to effect a change in capacitance. Since the change in capacitance remains persistent while the object remains on the layer, the presence of object can be continually detected even after it is released by the user.

Figure 9:
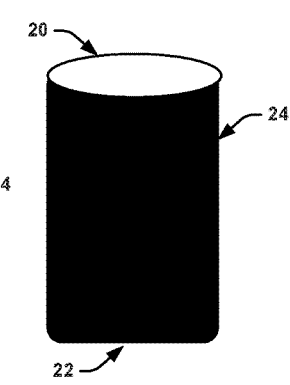

In some the examples, such as shown in FIGS. 1-5 and 8, the entire object or at least the outer surface thereof can be of electrically conductive material such that the contact can correspond to any part of the object's surface. A shown in FIG. 8, the object 20 can be made of a single unitary structure of an electrically conductive material. In the example of FIG. 9, at least a portion of the object 20 can be coated in a conductive material. The conductive material of the contact 24 can be any material (e.g., a metal like aluminum, stainless steel, platinum, gold, etc.) that can facilitate the transmission of an electric charge from the touch screen when the object is placed thereupon.

Figure 10:
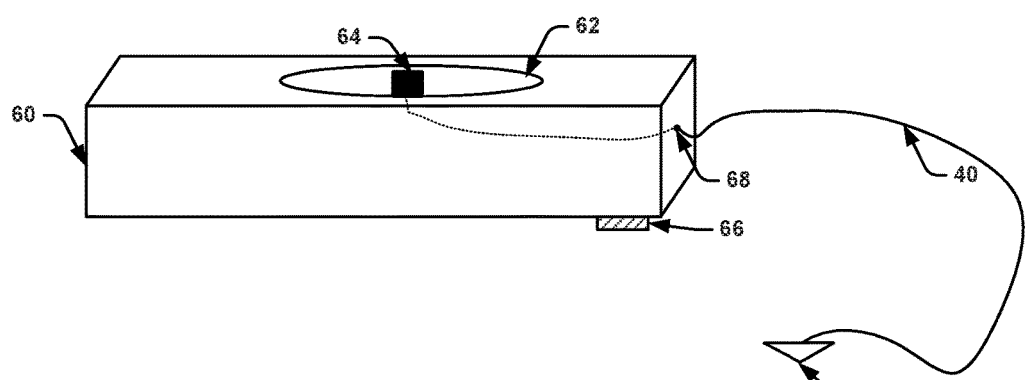
FIG. 10 depicts an example configuration of the housing that can be used in the detection of the object by the capacitive touch screen in the absence of human contact.

An example housing 60 is depicted in FIG. 10. As mentioned, the contact 24 of the object 20 can interface with a contact 64 of the housing 60 such that the electrically conductive path 40 extends from the object 20 to the housing 60. The housing can further include one or more electrically conductive paths that can be connected to extend beyond the housing 60. The housing 60 includes a substrate is that dimensioned and configured to cover at least a substantial portion of a touch screen when the housing 60 is placed on the touch screen. The substrate can be transparent so that the housing 60 does not obscure the touch screen and the screen is visible through the substrate. However, in situations where vision of the touch screen is unnecessary, the housing 60 can be opaque or semi-opaque. The housing 60 can also include an attachment mechanism 66 such that the housing 60 can be held attached to the touch screen when the housing 60 is placed on the touch screen. For example, the attachment mechanism 66 can include a material that establishes a removable attachment to the touch screen (e.g., an adhesive or a mechanical latch).

The substrate includes a sidewall portion that extends between opposing side surfaces of the substrate. One or more apertures 62 extends through the substrate between the first and second surfaces such that the surface of the touch screen is exposed through each aperture 62. The aperture 62 includes a contact 64 on an interior sidewall thereof. The aperture 62 is configured to receive the object 20 within the aperture such that the contact 24 of the object 20 interfaces with the contact 64 of the housing 80. Different configurations of the contact surface 22, as disclosed herein, can help facilitate the interface between contacts 24 and 64. The aperture 62 is further configured (e.g., a cylindrical throughhole) to support the object 20 to maintain the engagement between the contact surface 22 and the touch screen. In some examples, the housing can also include an electrical connector 68 that can establish portion of the electrical conductive path 40 between the contact 64 and a ground 86 (e.g., part of the touch screen device or electrical ground).

The support of the aperture 62 is especially important when the contact surface 22 is not flat (e.g., as shown in FIGS. 3-5). The aperture 62 can have an inner diameter sufficient to maintain the engagement between the contact surface 22 and the touch screen (e.g., the aperture 62 can have an inner diameter slightly greater than the outer diameter of the object 20. For instance, the inner diameter of the aperture 62 can be of a size such that object can freely fit therein so that the contact surface 22 can engage the touch screen when dropped or pushed into the aperture. Depending on the configuration of the contact surface, can tilt within the aperture 62 such that the contact 24 maintains contact with the contact 64 of the aperture 62. It will be understood that the aperture 62 need not be oval-shaped. Instead, the interior of the aperture 62 can be a shape that corresponds to the cross-sectional shape of the object 20 to facilitate the engagement between the contact surface 22 and the touch screen.

As mentioned, the housing 60 can include a plurality of apertures extending through the substrate between the first and second surfaces to expose the touch screen through the apertures. Each of the plurality of apertures can include a respective contact disposed along an interior sidewall, which contact can extend circumferentially a predetermined arc length up to the entire periphery of the aperture. An example of the housing 60 with two apertures 62a, 62b with corresponding contacts 64a, 64b is shown in FIGS. 11-13. The housing with the plurality of apertures can be used in connection with a plurality of objects, for example, when the touch screen possesses multi-touch capability (or the ability to detect two or more objects on the touch screen concurrently).

As depicted in FIGS. 11-13, the housing 60 with the two apertures 62a, 62b, each including corresponding contacts 64a, 64b, can have an electrical connection 64c that facilitates the flow of electrons between each the two contacts 64a, 64b to an end of the connection. Thus when an object, as disclosed herein, is inserted into a given aperture 62a, 62b, an electrical path is established from the contact surface of the object to the respective contact 64a, 64b and to the connector 68. The electrical connection 64c electrically connects each of the contacts to the connector to facilitate creating a corresponding electrical path, as disclosed herein. The housing 60 can be attached to the touch screen via attachment mechanisms 66a and/or 66b. It will be understood that the attachment mechanism is not confined to the extended rectangular shape as shown in FIG. 13. Instead, the attachment mechanism can be of a different shape or size that leads to the attachment of the housing 60 to the touch screen (e.g., tabs or feet).

Figure 14:
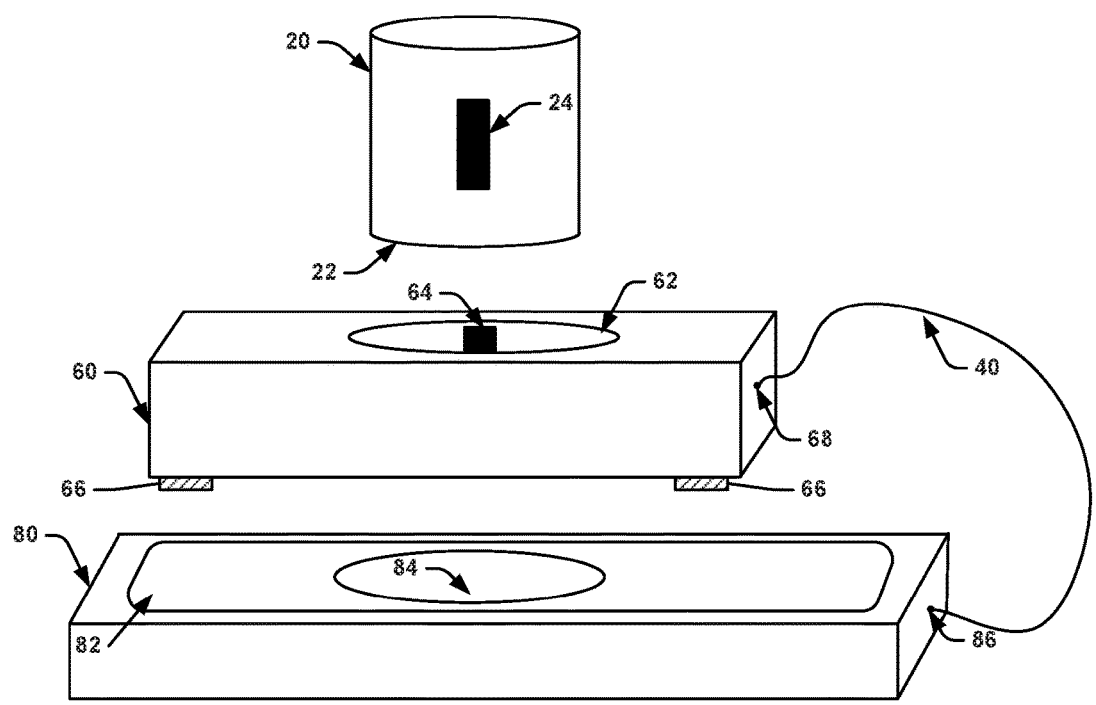
FIGS. 14 and 15 depict example systems that can facilitate the detection by a touch screen device of the object upon establishing an engagement with the touch screen in the absence of human contact.

FIG. 14 depicts an example isometric exploded view of a system 50 that includes an object 20, a housing 60 and a computing device 80. The object and housing provide a mechanism that enables the object 20 to be placed on a touch-sensitive surface 82 and supported by the housing 60 and still be detected by the touch screen in the absence of human contact. The touch-sensitive surface 82 provides a human-machine interface for the computing device 80.

Figure 15:
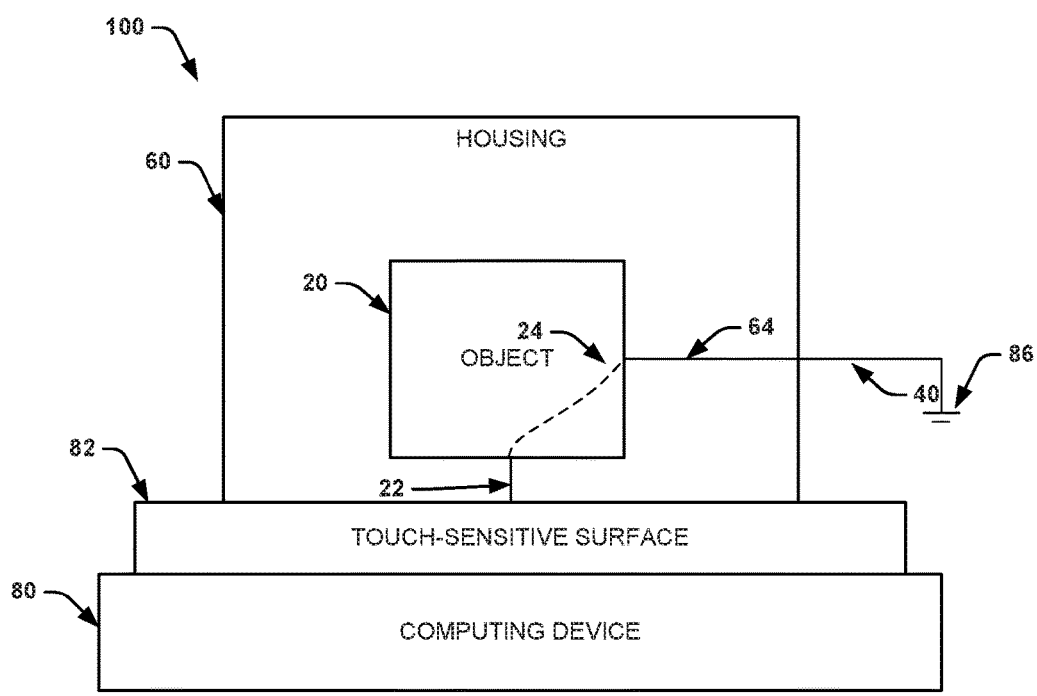

A schematic block diagram of the system 50 is depicted in FIG. 15. The touch screen device 80 (can include at least a memory that stores machine-readable instructions and a processor that accesses the memory for execution of the machine-readable instructions. The memory can be a nontransitory memory configured to store the machine readable instructions and/or data. The memory could be implemented, for example, as volatile memory (e.g., RAM), nonvolatile memory (e.g., a hard disk, flash memory, a solid state drive or the like) or combination of both. The processor (e.g., a processor core) can be configured in for accessing the memory and executing the machine-readable instructions. The device 80 can also include a controller that is able to determine the position of an object in response to detecting a change in capacitance in the touch screen.

By way of example, the memory can store a variety of machine-readable instructions and data, including an operating system, one or more application programs, other program modules, and program data. The one or more application programs can include user interface (HMI) that can respond to an engagement between the contact surface 22 of the object 20 and touch-sensitive surface 82. The user interface can be provided as including a graphical user interface (GUI) via a touch-sensitive surface or an associated display. The HMI can allow a user, such as a patient, to interact with the computing device 80. For example, the user can interact with the HMI through the object 20 that can be detected by the touch screen device 80 when engaged with the touch-sensitive surface 82 without requiring continuing contact by the user. Thus, when the user releases the object, it is still detected by the computing device 80 (e.g., by causing a detectable change in capacitance). As used herein, a user can refer to any living subject (e.g., adult or child), a physician, a physician assistant, a medical student, an advanced practice registered nurse, a veterinarian, a medical researcher, or another type of health care provider.

The GUI can include one or more GUI elements (e.g., HMI element 84 in FIG. 14) that are aligned with the one or more apertures (e.g., aperture 62 of the housing 60). The detection is based on the sufficient electron flow through the electrically conductive path. As an example, the GUI elements can include a graphic element 84 that can be rendered graphically by the touch screen 84 and seen through the aperture 62. If the housing is transparent, the graphic element can be seen through the housing as well. In response to detecting the engagement of the contact surface 22 of the object 20 and the surface 82, a processor can be programmed to change a visual aspect of the surface 82 (e.g., the color of graphic contact surface 82 can change) to indicate that the engagement is detected. This can vary depending on application requirements. The device 80 can also generate an audible sound in response to such contact.

When the contact surface 22 of the object 20 engages with the screen 82, the processor can detect the engagement due to a sensed change in capacitance that remains even in the absence of human contact with the object 20 (e.g., based on the sufficient flow of electrons through the electrically conductive path). As depicted in FIGS. 14 and 15, the electrically conductive path starts at the engagement between the contact surface 22 of the object 20, extends through the object 20 to contact 24. Contact 24 interfaces with contact 64 of the housing, and the path further extends to the electrical connector 68. The electrically conductive path 40 can extend from the housing 60 to the ground 86, which can be a port (e.g., a USB port, an audio output port, an audio input port or the like) on the touch screen device 80, a case of the touch screen device 80, a tether to the user or an earth ground source that is not affiliated with the touch screen device. In another embodiment, the electrically conductive path 40 can extend into the air a distance that can establish sufficient current flow to alter capacitance at the contact area and thereby enable the detection of the contact by the touch screen.

As a further example, the HMI elements can correspond to a medical test. The processor can be configured to determine a score related to the medical test based on a scoring function with the detection of the engagement between the contact surface 22 of the object 20 and the screen 82 as an input. The engagement can be located at the GUI element 84 can be seen through the aperture 62 of the housing 60. The score can correspond to a disease status represented by the medical test. The disease status can refer to a degree of progression of a disease, a diagnosis of a disease, an indication of normal function, a progress with regard to a training program, or the like. The score can be stored in the memory, and further analysis of the disease status can be undertaken based on the score. For example, the score can be combined with scores from other tests to create a complete score representing the disease status. The test data can also be transmitted to another computer via a network.

By way of further example, the medical test can be an upper extremity function test (e.g., a nine-hole peg test 9HPT) and the disease status can be related to multiple sclerosis. In this example, a pegboard (e.g., transparent plastic housing machined with a series of apertures) can be overlaid on a consumer electronics device with a capacitive touch screen (e.g., an iPad® or other tablet computer or computer having a touch screen). Objects (or markers, pegs, dowels of a conductive material) are placed in the holes of the pegboard, where they are allowed to touch the capacitive touch screen of the consumer electronics device. The consumer electronics device runs an application programmed to register each object as it touches or is removed from the screen. The fit between the objects and the apertures (or the contact of the aperture, such as a metal or other electrically conductive material bushing) is sufficiently close to provide a conductive link. In other examples, the objects need not physically touch the respective contacts of the apertures and, instead, can have a small air gap or other dielectric material (e.g., tape, film or the like) separating the objects and the contacts of the apertures to form a capacitor with one leg conductively linked to the touch screen and the other electrically grounded.

The contacts of the apertures in the housing are each linked to a ground source (e.g., the grounding pin of the 3.5 mm or other headphone jack of the consumer electronics device, the housing or an earth ground). Because a circuit is created between the touch screen and the ground (e.g., through the object and the housing), the capacitive touch screen can recognize the object as an input even after it is released by the user. As disclosed herein, in some instances, a sufficient circuit can be established in the absence of the object physically touching the contact of the aperture. For example, a small air gap or a piece of dielectric material can be disposed to separate the object 20 from the contact of the aperture. In this way the conductive link of the previous example is replaced with a capacitive coupling by using a dielectric material to separate the object and the contact. In this case, one side of the capacitor (the object 20) can be conductively linked to the touch screen and the other side of the capacitor (the contact of the aperture) can be electrically grounded.

Figure 16:
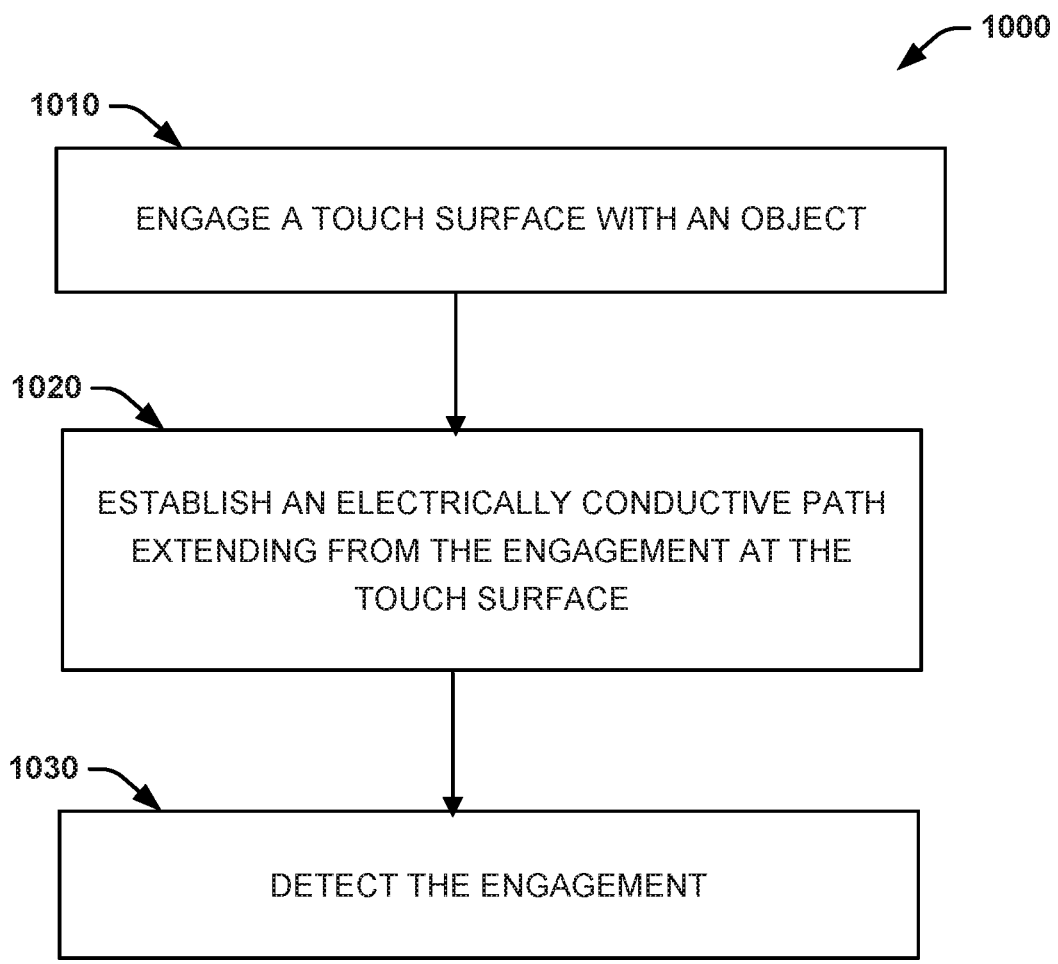
FIG. 16 depicts an example of a method for recognizing an engagement between an object and a capacitive touch screen in the absence of human contact.

In view of the foregoing structural and functional features described above, a method in accordance with various aspects of the present invention will be better appreciated with reference to FIG. 16. While, for purposes of simplicity of explanation, the method of FIG. 16 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention. It will be appreciated that some or all of each of these methods can be implemented as machine-readable instructions on a non-transitory computer readable medium. The machine-readable instructions can be provided to the processor (e.g., of the touch screen device) to produce a machine, for execution, such that the instructions can implement the functions specified in the blocks of the flowchart depicting the method 1000.

FIG. 16 illustrates an example of a method 1000 for recognizing an engagement between an object (e.g., object 20, as shown in any one of FIGS. 1-9, 14, and 15) and a touch screen (e.g., touch screen 80, as shown in any one of FIGS. 14 and 15) in the absence of human contact. At 1010, the touch screen is engaged with a contact surface of an object (e.g., contact surface 22, as shown in any one of FIGS. 1-9, 14, and 15). At 1020, an electrically conductive path (e.g., path 40, as shown in any one of FIGS. 1, 10, 14, and 15) is established that extends from the engagement of the contact surface and the touch screen to a termination (e.g., in air or an electrical ground). The electrically conductive path allows for electrons (in an amount sufficient for detection) to flow through the electrically conductive path in the absence of human contact. At 1030, the engagement of the contact surface and the touch screen is detected (e.g., by a device associated with the touch screen that includes a non-transitory memory and a processor), such as based on a change in capacitance detected at the point or points of contact between each object placed on the screen through the housing. In some instances, an electrically conductive portion of each object can physically engage with an electrically conductive portion of the housing. In other instances, each object need not touch the electrically conductive portion of the housing. For example, a small air gap or a piece of dielectric material can separate the object 20 from the contact 24 with a dielectric material creating a capacitive coupling between the object and the contact. Thus, in this case, one side of the capacitor (the object) can be conductively linked to the touch screen and the other side of the capacitor (the contact of the corresponding aperture of the housing) can be electrically grounded.

In view of the foregoing, the device, system and methods disclosed herein can be used in assessing upper extremity function in various disease populations. Such use can provide additional data to support research and rehab when compared to the standard testing (e.g., standard 9 hole peg test). For example, when used with a touch screen device, clinicians and researchers can break the complex task of upper extremity function in to finer resolution data points such as grasping, insertion of pegs, removal of pegs and upper extremity movement speeds. From these additional data, innovative outcome measures can be developed such as the ratio of insertion versus removal time, learning or fatigue throughout the course of the assessment or pattern of peg insertion and removal.

Additionally, a dual-task upper extremity and cognition task that could easily be built around the same apparatus. Such combined testing can render graphical a moving target that the patient would need to follow by placing pegs on the screen. Further, this approach could be used to facilitate the use of assistive devices for those with movement disorders or upper extremity amputee's as their fixture typically do not register on capacitive screens. Such applications have demand from biomechanics, rehab and drug therapy perspectives.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system for performing a medical test, comprising:
   a computing device comprising a touch-sensitive touch screen defining an interface;
   a housing comprising a substrate dimensioned and configured to cover at least a substantial portion of the touch-sensitive touch screen when placed thereon, a plurality of apertures extending through the substrate, wherein the touch-sensitive touch screen is exposed through at least one of the plurality of apertures; and
   an object configured for insertion through the at least one of the plurality of apertures to engage a portion of the touch-sensitive touch screen,
   wherein the plurality of apertures are configured to receive the object therein and to maintain an engagement between a distal end of the object and the touch-sensitive touch screen;
   wherein an electrically conductive path extends from the distal end of the object contacting the touch-sensitive touch screen, through at least one contact of the at least one of the plurality of apertures and is configured to provide for sufficient electrons to flow from the touch-sensitive touch screen through the electrically conductive path to a port of the computing device to enable detection of the object contacting the touch-sensitive touch screen in the absence of human contact with the object.

2. The system of claim 1, further comprising an attachment mechanism configured to removably attach the housing to the computing device comprising the touch-sensitive touch screen.

3. The system of claim 1, wherein the electrical connection comprises a capacitive coupling between the object and the at least one contact, wherein the object is conductive and the at least one contact is electrically grounded.

4. A method for performing a medical test, comprising:
   engaging a touch-sensitive surface of a computing device with an object inserted through an aperture of a housing,
   wherein the housing is sized and dimensioned to cover at least a portion of the touch-sensitive surface and configured to stabilize the object when inserted through the aperture;
   forming an electrical connection between a contact within the aperture and a contact on an exterior surface of the object; and
   establishing an electrically conductive path from the touch-sensitive surface to the contact of the aperture and extending a distance beyond the contact of the aperture, such that the electrically conductive path allows for sufficient electrons to flow from the touch-sensitive surface through the electrically conductive path to enable detection of the engagement by the touch-sensitive surface of the computing device in absence of human contact with the object during such engagement.

5. The system of claim 1, wherein the housing comprises a plurality of apertures extending through the substrate, each of the plurality of apertures exposes a respective portion of the touch-sensitive touch screen,
   wherein each of the plurality of apertures is configured to receive and support another object.

6. The system of claim 1, where each of the plurality of apertures comprises an electrical contact disposed along the interior that connects to an electrical ground relative to the touch-sensitive touch screen of the computing device to detect insertion of the object therein when the object contacts the touch-sensitive touch screen.

7. The system of claim 1, wherein the electrically conductive path is configured to establish an electrical ground potential relative to the touch-sensitive touch screen.

8. The method of claim 4, wherein at least a portion of the contact on the exterior surface of the object comprises a conductive material.

9. The method of claim 4, wherein the engaging further comprises placing a non-flat portion of the object into contact with the touch screen of the computing device so that the object is imbalanced.

10. The method of claim 4, wherein the engaging further comprises contacting an interface element of the touch-sensitive surface with a portion of the object.

11. The method of claim 10, further comprising detecting, by the computing device associated with the touch-sensitive surface comprising a processor, the engagement between the portion of the object and the touch-sensitive surface based on an electron flow through the electrically conductive path.

12. The method of claim 11, wherein the interface element is one of a plurality of interface elements corresponding to a medical test, and
further comprising determining, by the computing device, a score for the medical test based on the engagement.

13. The method of claim 12, wherein the medical test comprises a nine-hole peg test.

14. The method of claim 12, wherein results of the medical test are based on the electron flow responsive to the engagement between the portion of the object and the touch-sensitive surface.

15. The method of claim 4, further comprising attaching the housing to the touch-sensitive surface of the computing device by a removable attachment mechanism.

16. The method of claim 4, wherein the engaging further comprises a distal portion of the object contacts the touch-sensitive surface.

17. The method of claim 16, wherein the contact surface of the object is on the distal portion of the object.

18. The method of claim 4, further comprising engaging the touch-sensitive surface of the computing device with another object inserted through another aperture of the housing.

19. The method of claim 18, further comprising another electrical connection between another contact and the exterior surface of the other object and the other contact within the other aperture.

20. The method of claim 19, further comprising establishing another electrically conductive path from the touch-sensitive surface to the contact of the other object to the contact of the other aperture and extending a distance beyond the contact of the other aperture, such that the electrically conductive path extends the distance beyond the other contact of the aperture to allow for sufficient electrons to flow from the touch-sensitive surface through the electrically conductive path to enable detection of the another engagement by the touch-sensitive surface of the computing device in absence of human contact with the other object during such engagement.

* * * * *